(12) United States Patent
Uemura et al.

(10) Patent No.: US 7,029,909 B1
(45) Date of Patent: Apr. 18, 2006

(54) PROTEIN EXPRESSION VECTOR AND UTILIZATION THEREOF

(75) Inventors: Hidetoshi Uemura, Itami (JP); Akira Okui, Yamatokoriyama (JP); Katsuya Kominami, Hannan (JP); Nozomi Yamaguchi, Kyoto (JP); Shinichi Mitsui, Kyoto (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/856,050

(22) PCT Filed: Nov. 19, 1999

(86) PCT No.: PCT/JP99/06474

§ 371 (c)(1),
(2), (4) Date: May 17, 2001

(87) PCT Pub. No.: WO00/31284

PCT Pub. Date: Jun. 2, 2000

(30) Foreign Application Priority Data

Nov. 20, 1998 (JP) .................................. 10/331515

(51) Int. Cl.
| | |
|---|---|
| *C12N 15/00* | (2006.01) |
| *C12N 5/06* | (2006.01) |
| *C12N 5/00* | (2006.01) |
| *C12N 1/20* | (2006.01) |

(52) U.S. Cl. .................... 435/320.1; 435/348; 435/325; 435/252.3; 435/69.1

(58) Field of Classification Search ............. 435/320.1, 435/69.1, 219, 325, 348, 252.3
See application file for complete search history.

(56) References Cited

FOREIGN PATENT DOCUMENTS

JP          10179169 A1     7/1998

OTHER PUBLICATIONS

New England Biolabs 1995 Catalog, pp. 140-141.*
Invitrogen 1997 Catalog, pp. 12 and 37.*
Glick et al., Molecular Biotechnology: Principles and Applications of Recombinant DNA, 1994.*
Yamashiro et al., Biochimica et Biophysica Acta 1350(1): 11-14, 1997.*
Sabine K. et al., "The baculovirus expression vector pBSV-8His directs secretion of histidine-tagged proteins" Gene, vol. 162, (1995), pp. 225-229.
Chubet, Richard et al; "Vectors for Expression and secretion of FLAG epitope-tagged proteins in mammalian cells"; *Biotechniques*, vol. 20, No. 1, pp. 136-141; 1996.
Hosfield, T. et al; "Versatile epitope tagging vector for gene expression in mammalian cells"; *Biotechniques*; vol. 25, No. 2, pp. 306-309; 1998.
Morganti. L. et al; "Production and characterization of biologically active Ala-Ser-(His)-6-Ile-Glu-Gly-Arg-human prolactin (tag-hpRL) secreted in the periplasmic space of Escherichia coli"; *Biotechnology and Applied Biochemistry*; vol. 23, No. 1, pp. 67-75, 1996.
Morganti, L. et al; "Synthesis and characterization of recombinant authentic human prolactin secreted intothe periplasmic space of Escherichia Coli"; *Biotechnology and Applied Biochemistry*; vol. 27; No. 1, pp. 63-70, 1998.
Nilsson, J. et al; "Affinity fusion strategies of detection, purification, and immobilization of recombinant proteins"; *Protein Expression and Purification*, vol. 11, No. 1, pp. 1-16, 1997.

* cited by examiner

*Primary Examiner*—Rebecca E. Prouty
*Assistant Examiner*—Delia M. Ramirez
(74) *Attorney, Agent, or Firm*—Browdy and Neimark, PLLC

(57) ABSTRACT

A protein expression vector containing (a) a nucleotide sequence encoding an IgG(κ) or a trypsin secretory signal peptide, (b) a nucleotide sequence encoding a polyhistidine amino acid sequence, (c) a nucleotide sequence encoding an amino acid sequence comprising amino acid residues 36–40 of SEQ ID NO:19 (Asp-Asp-Asp-Asp-Lys), which is cleavable by an enterokinase, and (d) a cloning site into which a nucleotide sequence encoding a target protein can be inserted, wherein (a), (b), (c) and (d) are assembled within the vector in the order recited.

3 Claims, 8 Drawing Sheets

Fig. 2
1  2
1; cell extract
2; culture supernatant 1 2 3

1; pSecTag/neurosin
2; pSecHisTag/neurosin
3; pSecTrypHis/neurosin 1  2

1; culture supernatant

2; cell extract

1; pass

2; 5 mM imidazole

3; 10 mM imidazole

4; 100 mM imidazole

5; 500 mM imidazole

SEQUENCE LISTING

<160> NUMBER OF SEQ ID NOS: 22

<210> SEQ ID NO 1
<211> LENGTH: 117
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide to construct plasmid
      pTrypHis

<400> SEQUENCE: 1
aagcttggct agcaacacca tgaatctact cctgatcctt acctttgttg ctgctgctgt    60
tgctgccccc tttcaccatc accatcacca tgacgacgat gacaaggatc cgaattc     117

<210> SEQ ID NO 2
<211> LENGTH: 117
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide to construct plasmid
      pTrypHis

<400> SEQUENCE: 2
gaattcggat ccttgtcatc gtcgtcatgg tgatggtgat ggtgaaaggg ggcagcaaca    60
gcagcagcaa caaaggtaag gatcaggagt agattcatgg tgttgctagc caagctt     117

<210> SEQ ID NO 3
<211> LENGTH: 15
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify
      neurosin-encoding sequence

<400> SEQUENCE: 3
ttggtgcatg gcgga                                                    15

<210> SEQ ID NO 4
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify
      neurosin-encoding sequence

<400> SEQUENCE: 4
ggaattcact tggcctgaat                                               20

<210> SEQ ID NO 5
<211> LENGTH: 26
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid pTrypHis/Neurosin

```
<400> SEQUENCE: 5
ctaagcttga cgacgatgac aagttg                                            26

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
tcctcgagac ttggcctgaa tggtttt                                           27

<210> SEQ ID NO 7
<211> LENGTH: 26
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid pTrypHis/Neurosin

<400> SEQUENCE: 7
ccaagcttca ccatcaccat caccat                                            26

<210> SEQ ID NO 8
<211> LENGTH: 99
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide to construct plasmid
      pSecTrypHis

<400> SEQUENCE: 8
aagcttggct agcaacacca tgaatctact cctgatcctt acctttgttg ctgctgctgt       60
tgctgccccc tttgacgacg atgacaagga tccgaattc                              99

<210> SEQ ID NO 9
<211> LENGTH: 99
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide to construct plasmid
      pSecTrypHis

<400> SEQUENCE: 9
gaattcggat ccttgtcatc gtcgtcaaag ggggcagcaa cagcagcagc aacaaaggta       60
aggatcagga gtagattcat ggtgttgcta gccaagctt                              99

<210> SEQ ID NO 10
<211> LENGTH: 35
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid pSecTrypHis/Neurosin

<400> SEQUENCE: 10
gcgctagcag atctccatga atctactcct gatcc                                  35
```

<210> SEQ ID NO 11
<211> LENGTH: 29
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid pSecTrypHis/Neurosin

<400> SEQUENCE: 11
tgaagcttgc catggaccaa cttgtcatc                                    29

<210> SEQ ID NO 12
<211> LENGTH: 17
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid pTrypSigTag

<400> SEQUENCE: 12
gcacagtcga ggctgat                                                 17

<210> SEQ ID NO 13
<211> LENGTH: 17
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid pFBTrypSigTag

<400> SEQUENCE: 13
caaatgtggt atggctg                                                 17

<210> SEQ ID NO 14
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION:

<400> SEQUENCE: 14

```
ttg gtg cat ggc gga ccc tgc gac aag aca tct cac ccc tac caa gct      48
Leu Val His Gly Gly Pro Cys Asp Lys Thr Ser His Pro Tyr Gln Ala
1               5                   10                  15 gcc ctc tac acc tcg ggc cac ttg ctc tgt ggt ggg tca ctt atc cat      96
Ala Leu Tyr Thr Ser Gly His Leu Leu Cys Gly Gly Val Leu Ile His
                20                  25                  30 cca ctg tgg gtc ctc aca gct gcc cac tgc aaa aaa ccg aat ctt cag     144
Pro Leu Trp Val Leu Thr Ala Ala His Cys Lys Lys Pro Asn Leu Gln
            35                  40                  45 gtc ttc ctg ggg aag cat aac ctt cgg caa agg gag agt tcc cag gag     192
Val Phe Leu Gly Lys His Asn Leu Arg Gln Arg Glu Ser Ser Gln Glu
        50                  55                  60 cag agt tct gtt gtc cgg gct gtg atc cac cct gac tat gat gcc gcc     240
Gln Ser Ser Val Val Arg Ala Val Ile His Pro Asp Tyr Asp Ala Ala
65                  70                  75                  80 agc cat gac cag gac atc atg ctg ttg cgc ctg gca cgc cca gcc aaa     288
```

-continued

```
Ser His Asp Gln Asp Ile Met Leu Leu Arg Leu Ala Arg Pro Ala Lys
             85                  90                  95 ctc tct gaa ctc atc cag ccc ctt ccc ctg gag agg gac tgc tca gcc      336
Leu Ser Glu Leu Ile Gln Pro Leu Pro Leu Glu Arg Asp Cys Ser Ala
            100                 105                 110 aac acc acc agc tgc cac atc ctg ggc tgg ggc aag aca gca gat ggt      384
Asn Thr Thr Ser Cys His Ile Leu Gly Trp Gly Lys Thr Ala Asp Gly
            115                 120                 125 gat ttc cct gac acc atc cag tgt gca tac atc cac ctg gtg tcc cgt      432
Asp Phe Pro Asp Thr Ile Gln Cys Ala Tyr Ile His Leu Val Ser Arg
        130                 135                 140 gag gag tgt gag cat gcc tac cct ggc cag atc acc cag aac atg ttg      480
Glu Glu Cys Glu His Ala Tyr Pro Gly Gln Ile Thr Gln Asn Met Leu
145                 150                 155                 160 tgt gct ggg gat gag aag tac ggg aag gat tcc tgc cag ggt gat tct      528
Cys Ala Gly Asp Glu Lys Tyr Gly Lys Asp Ser Cys Gln Gly Asp Ser
                165                 170                 175 ggg ggt ccg ctg gta tgt gga gac cac ctc cga ggc ctt gtg tca tgg      576
Gly Gly Pro Leu Val Cys Gly Asp His Leu Arg Gly Leu Val Ser Trp
            180                 185                 190 ggt aac atc ccc tgt gga tca aag gag aag cca gga gtc tac acc aac      624
Gly Asn Ile Pro Cys Gly Ser Lys Glu Lys Pro Gly Val Tyr Thr Asn
        195                 200                 205 gtc tgc aga tac acg aac tgg atc caa aaa acc att cag gcc aag tga      672
Val Cys Arg Tyr Thr Asn Trp Ile Gln Lys Thr Ile Gln Ala Lys
    210                 215                 220
```

<210> SEQ ID NO 15
<211> LENGTH: 223
<212> TYPE: PRT
<213> ORGANISM: Homo sapiens
<220> FEATURE:
<223> OTHER INFORMATION: Synthetic

<400> SEQUENCE: 15

```
Leu Val His Gly Gly Pro Cys Asp Lys Thr Ser His Pro Tyr Gln Ala
1               5                   10                  15

Ala Leu Tyr Thr Ser Gly His Leu Leu Cys Gly Gly Val Leu Ile His
            20                  25                  30

Pro Leu Trp Val Leu Thr Ala Ala His Cys Lys Lys Pro Asn Leu Gln
        35                  40                  45

Val Phe Leu Gly Lys His Asn Leu Arg Gln Arg Glu Ser Ser Gln Glu
    50                  55                  60

Gln Ser Ser Val Val Arg Ala Val Ile His Pro Asp Tyr Asp Ala Ala
65                  70                  75                  80

Ser His Asp Gln Asp Ile Met Leu Leu Arg Leu Ala Arg Pro Ala Lys
                85                  90                  95

Leu Ser Glu Leu Ile Gln Pro Leu Pro Leu Glu Arg Asp Cys Ser Ala
            100                 105                 110

Asn Thr Thr Ser Cys His Ile Leu Gly Trp Gly Lys Thr Ala Asp Gly
        115                 120                 125

Asp Phe Pro Asp Thr Ile Gln Cys Ala Tyr Ile His Leu Val Ser Arg
    130                 135                 140

Glu Glu Cys Glu His Ala Tyr Pro Gly Gln Ile Thr Gln Asn Met Leu
145                 150                 155                 160

Cys Ala Gly Asp Glu Lys Tyr Gly Lys Asp Ser Cys Gln Gly Asp Ser
                165                 170                 175

Gly Gly Pro Leu Val Cys Gly Asp His Leu Arg Gly Leu Val Ser Trp
```

```
                180              185             190
Gly Asn Ile Pro Cys Gly Ser Lys Glu Lys Pro Gly Val Tyr Thr Asn
        195                 200             205

Val Cys Arg Tyr Thr Asn Trp Ile Gln Lys Thr Ile Gln Ala Lys
    210                 215             220

<210> SEQ ID NO 16
<211> LENGTH: 135
<212> TYPE: DNA
<213> ORGANISM: Homo sapiens
<220> FEATURE:
<221> NAME/KEY: CDS
<222> LOCATION: (1)..(135)
<223> OTHER INFORMATION:

<400> SEQUENCE: 16 atg gag aca gac aca ctc ctg cta tgg gta ctg ctg ctc tgg gtt cca       48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcg cgc cgt acg       96
Gly Ser Thr Gly Asp Ala Ala Gln Pro Ala Arg Arg Ala Arg Arg Thr
            20                  25                  30 aag ctt cac cat cac cat cac cat gac gac gat gac aag                  135
Lys Leu His His His His His His Asp Asp Asp Asp Lys
        35                  40                  45

<210> SEQ ID NO 17
<211> LENGTH: 45
<212> TYPE: PRT
<213> ORGANISM: Homo sapiens
<220> FEATURE:
<223> OTHER INFORMATION: Synthetic

<400> SEQUENCE: 17

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu His His His His His His Asp Asp Asp Asp Lys
        35                  40                  45

<210> SEQ ID NO 18
<211> LENGTH: 120
<212> TYPE: DNA
<213> ORGANISM: Homo sapiens
<220> FEATURE:
<221> NAME/KEY: CDS
<222> LOCATION: (1)..(120)
<223> OTHER INFORMATION:

<400> SEQUENCE: 18 atg aat cta ctc ctg atc ctt acc ttt gtt gca gct gct gtt gct gcc       48
Met Asn Leu Leu Leu Ile Leu Thr Phe Val Ala Ala Ala Val Ala Ala
1               5                   10                  15 ccc ttt gat gat gat gac aag ttg gtg cat ggc aag ctt cac cat cac       96
Pro Phe Asp Asp Asp Asp Lys Leu Val His Gly Lys Leu His His His
            20                  25                  30 cat cac cat gac gac gat gac aag                                      120
His His His Asp Asp Asp Asp Lys
        35                  40

<210> SEQ ID NO 19
<211> LENGTH: 40
<212> TYPE: PRT
```

-continued

```
<213> ORGANISM: Homo sapiens
<220> FEATURE:
<223> OTHER INFORMATION: Synthetic

<400> SEQUENCE: 19

Met Asn Leu Leu Leu Ile Leu Thr Phe Val Ala Ala Val Ala Ala
1               5                   10                  15

Pro Phe Asp Asp Asp Asp Lys Leu Val His Gly Lys Leu His His His
                20                  25                  30

His His His Asp Asp Asp Asp Lys
            35              40

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Leu Val Pro Arg Gly Ser
1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic

<400> SEQUENCE: 21

Ile Glu Gly Arg
1

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Glu Asn Leu Tyr Phe Gln
1               5
```

PROTEIN EXPRESSION VECTOR AND UTILIZATION THEREOF

REFERENCE TO RELATED APPLICATIONS

The present application is the national stage under 35 U.S.C. §371 of international application PCT/JP99/06474, filed 19 Nov. 1999 which designated the United States, and which application was not published in the English language.

FIELD OF THE INVENTION

The present invention relates to a protein expression vector and use thereof. More particularly, it relates to a protein expression vector which can express a gene encoding a target protein in various hosts to produce said protein. The present invention is advantageous and characterized technically in that a target protein can be expressed in a state of a recombinant fusion protein that is easy to be purified and is secreted extracellularly as well as in that a target protein can be obtained eventually in a state where the N-terminus of the target protein is free of addition of any extra amino acid.

BACKGROUND OF THE INVENTION

A variety of expression vectors have heretofore been developed for using in the production of recombinant proteins. In particular, for the expression systems utilizing microorganisms such as *Escherichia coli* and yeast as hosts, there have been provided those which are expected to give high yields. In the case of proteins whose biological activity depends on sugar chains, it is necessary to produce such proteins by using animal cells as the host. In this regard, recently, a vector which permits a high level expression has also been developed (JP 10-179169 A), and there is an example of successful expression of human mannan binding protein by using this vector.

Thus, systems utilizing *Escherichia coli*, yeast or animal cells have been used by many investigators in order to produce foreign proteins. In the systems utilizing *Escherichia coli* as the host, expressing capacity can be enhanced by using a potent promoter derived from *Escherichia coli*. However, in most cases, foreign proteins expressed accumulate within cells as inclusion bodies. Therefore, it is necessary to solubilize the protein by using a denaturing agent such as urea and guanidine and then to unwind the protein to the native form. Then, it is extremely difficult to directly isolate and purify the protein in the active form, and complicated procedures are required.

Further, in the system utilizing yeast as the host, a proteolytic degradation is unavoidable. Then, improvement in the expression of soluble proteins can not be expected. In addition, the proteins are modified in a different way because of remarkably different expressing environment from the intercellular environment of higher animals. Furthermore, although systems utilizing animal cells may allow the production of recombinant proteins in forms comparable to natural ones, complicated procedures are needed, thereby having a drawback with respect to production efficiency.

In recent years, an expression system has received an attention, wherein insect cells are used as the host infected with a baculovirus. The reason for this is, for example, that the baculovirus, upon infecting insect cells, produces more than approximately 25% of the total cell protein as a polyhedron protein, and a high expression system for foreign proteins has been developed by using this potent promoter. And, the following advantages have been recognized in regard to the production of foreign proteins by using a baculovirus-insect cell expression system: (a) the expression levels of foreign proteins are high; (b) processing of signal peptides, modification with sugar chains, phosphate, lipids, etc., dimerization, virion formation, intron splicing, and the like take place as those in natural proteins; (c) the intracellular localization of protein within insect cells is the same as that with the natural protein; (d) insect cells can be cultivated in a suspension culture.

Heretofore, a variety of proteins (e.g., insulin, interferons, erythropoietin, mannan binding protein, conglutinin, etc.) have been produced in insect cells and animal cells by using gene engineering technology. In order to obtain recombinant proteins with quality comparable to that of the natural form, an expression system utilizing animal cells (e.g., mammalian cells or insect cells) as hosts is essential as described above. Then, the development of expression vectors which are useful in said expression system has been desired.

The development of expression vectors has been attempted primarily along two approaches, namely an attempt to enhance the expression level of recombinant proteins, and an attempt to simplify the purification of expressed recombinant proteins. Vectors which aim at enhancing the expression level include, for example, the vector disclosed in JP 10-179169 A. As vectors which aim at enhancing the purification efficiency, histidine Tag vector (manufactured by Invitrogen Corporation) is known.

pSecTag vector (manufactured by Invitrogen Corporation) is commercially available as a vector which facilitates purification of recombinant proteins secreted extracellularly. This vector is used with animal cells as the host, and contains a secretory signal, a multicloning site capable of inserting a nucleotide sequence encoding a target protein, a myc epitope which recognizes a fusion protein, and a polyhistidine Tag which allows purification of the protein by a nickel chelate resin. However, this vector can not express a target protein in insect cells. Also, even if a protein is expressed in animal cells, amino acids such as myc epitope and histidine Tag are added to the C-terminus of a target protein, precluding the protein from being obtained as a pure recombinant protein, which is a drawback of using this vector.

On the other hand, pFastBAC HT vector (manufactured by GIBCO BRL) is commercially available as a vector which enables proteins to be expressed in insect cells and to be purified easily. This vector uses insect cells as the host and contains a histidine Tag nucleotide sequence, a cleavable nucleotide sequence which allows the cleavage of the sequence between that encoding the histidine Tag sequence and that encoding a target protein, and a multicloning site capable of inserting the nucleotide sequence encoding the target protein. However, this vector does not contain a secretory signal which enables extracellular secretion of a target protein to. Therefore, cells must be disrupted in order to obtain a target protein expressed intracellularly. A myriad of proteins within the cells will be released by cell disruption, making it extremely difficult to purify the target protein.

Also, it is desirable that an expressible recombinant protein is identical to the corresponding natural protein in its amino acid sequence, with no expression vector-derived amino acids being added to the C-terminus or the N-terminus. In particular, it has been known that the type of the amino acid at position 1 (N-terminus) of a natural or recombinant protein markedly affects the stability of said protein. That is, there is a strong correlation between the property of the N-terminal amino acid and the in vivo half life of the protein, which is designated as the N-end rule. This correlation holds true to a greater or lesser extent with proteins of every living system that has been so far studied spanning from bacteria to mammals.

Under the above-described circumstances, it has been desired to develop an expression vector that can express recombinant proteins in an expression system which can utilize animal cells, mammalian cells or insect cells in particular, as the host and can secrete the protein extracellularly, wherein the obtained recombinant can be purified by a simple procedure, and still further at least the N-terminus of the amino acid sequence of the recombinant protein is identical to that of the natural protein.

OBJECTS OF THE INVENTION

Accordingly, the primary object of the present invention is to provide a novel expression vector which can express recombinant proteins in various hosts such as animal cells, particularly, mammalian cells or insect cells, and can secrete the proteins extracellularly, wherein the obtained recombinant can be purified by a simple procedure, and still further at least the N-terminus of the amino acid sequence of the recombinant protein is identical to that of the natural protein.

SUMMARY OF THE INVENTION

The present invention provides an expression vector which, upon insertion into various host cells (particularly animal cells such as mammalian cells and insect cells), can secrete a recombinant protein produced extracellularly, allows the simple purification of the produced recombinant protein, and still further provides the recombinant protein almost identical in quality to the natural protein. The expression vector provided herein may also be used in situations where it is preferred to use microorganisms and the like as the host, for example, where the presence of sugar chains on the protein is not necessary, or protein production is carried out as a basic study.

The protein expression vector of the present invention contains as the basic construction at least (1) a nucleotide sequence for a secretory signal and, in the 3' downstream side thereof, (2) a nucleotide sequence for Tag, (3) a cleavable nucleotide sequence, and (4) a nucleotide sequence encoding a target protein or (4') a cloning site into which a target protein-encoding nucleotide sequence can be inserted, in this order. The vector may also contain, as appropriate, an optional nucleotide sequence such as a nucleotide sequence encoding an epitope or a nucleotide sequence encoding a spacer sequence before, after or between the essential nucleotide sequences of (1) through (4) or (4').

That is, according to the present invention, there is provided:

(1) A protein expression vector comprising a secretory nucleotide signal and, in the 3' downstream side thereof, a Tag nucleotide sequence, a cleavable nucleotide sequence and a cloning site into which a nucleotide sequence encoding a target protein can be inserted, in this order;
(2) The protein expression vector according to the above (1), wherein a nucleotide sequence encoding a target protein is inserted in the cloning site;
(3) The protein expression vector according to the above (1) or (2), wherein the cloning site or the nucleotide sequence encoding the target protein is present successively at the 3' end of the cleavable nucleotide sequence;
(4) The protein expression vector according to any one of the above (1) to (3), wherein a nucleotide sequence encoding at least on amino acid is contained as a spacer nucleotide sequence in the 3' downstream side of the secretory signal nucleotide sequence, but in the 5' upstream side of the cleavable nucleotide sequence;
(5) The protein expression vector according to the above (4), wherein the spacer nucleotide sequence is anucleotide sequence encoding at least the amino acid sequence of Leu-Val-His-Gly-Lys-Leu (amino acid 24–29 of SEQ ID NO:19);
(6) The protein expression vector according to the above (4) or (5), wherein the spacer nucleotide sequence is composed of at least a cleavable nucleotide sequence;
(7) The protein expression vector according to any one of the above (1) to (6), wherein the cleavable nucleotide sequence, when translated into an amino acid sequence, is cleaved by an enzyme at immediate upstream and/or immediate downstream and/or in the middle of said amino acid sequence;
(8) The protein expression vector according to the above (7), wherein the cleavable nucleotide sequence is a nucleotide sequence encoding at least the amino acid sequence of Asp-Asp-Asp-Asp-Lys (amino acid 19–23 of SEQ ID NO:19);
(9) The protein expression vector according to the above (7) or (8), wherein the enzyme is enterokinase;
(10) The protein expression vector according to any one of the above (1) to (9), wherein the secretory signal nucleotide sequence is IgG (K) signal or trypsin signal;
(11) The protein expression vector according to any one of the above (1) to (10), wherein the Tag nucleotide sequence is polyhistidine;
(12) The protein expression vector according to any one of the above (1) to (11) further comprising a nucleotide sequence encoding an antibody recognition epitope;
(13) The protein expression vector according to any one of the above (1) to (12), wherein the nucleotide sequence encoding the target protein is that encoding neurosin;
(14) Host cells transformed with the protein expression vector according to any one of the above (1) to (13);
(15). The host cells according to the above (14) which are animal cells;
(16) The host cells according to the above (15), wherein the animal cells are mammalian cells;
(17) The host cells according to the above (15), wherein the animal cells are insect cells;
(18) A process for producing a target protein which comprises using the protein expression vector or the host cells according to any one of the above (1) to (18);
(19) A target protein which is obtained by the process according to the above (18);
(20) A process for producing a recombinant fusion protein comprising an amino acid sequence of a target protein which comprises using the protein expression vector or the host cells according to any one of the above (1) to (18);
(21) A recombinant fusion protein comprising the amino acid sequence of the target protein obtained by the process according to the above (20);
(22) A process for producing a target protein which comprises retaining the recombinant fusion protein according to the above (21) with a substance capable of recognizing Tag and/or an epitope in said recombinant fusion protein, liberating the recombinant fusion protein from the substance to purify it, and releasing the target protein by reacting said purified recombinant fusion protein with an enzyme capable of recognizing the cleavable site within said recombinant fusion protein, followed by collecting the released target protein;

(23) A process for producing a target protein, which comprises retaining the recombinant fusion protein according to the above (21) with a substance capable of recognizing Tag and/or an epitope in said recombinant fusion protein, and releasing the target protein by reacting said purified recombinant fusion protein with an enzyme capable of recognizing the cleavable site within said recombinant protein, followed by collecting the released target protein; and

(24) A target protein is obtained by the process according to the above (22) or (23).

BRIEF DESCRIPTION OF THE DRAWINS

FIG. 2 illustrates the western blot analysis of the culture supernatant and the cell extract obtained in Example 1.

DETAILED DESCRIPTION OF THE INVENTION

Figure 1:
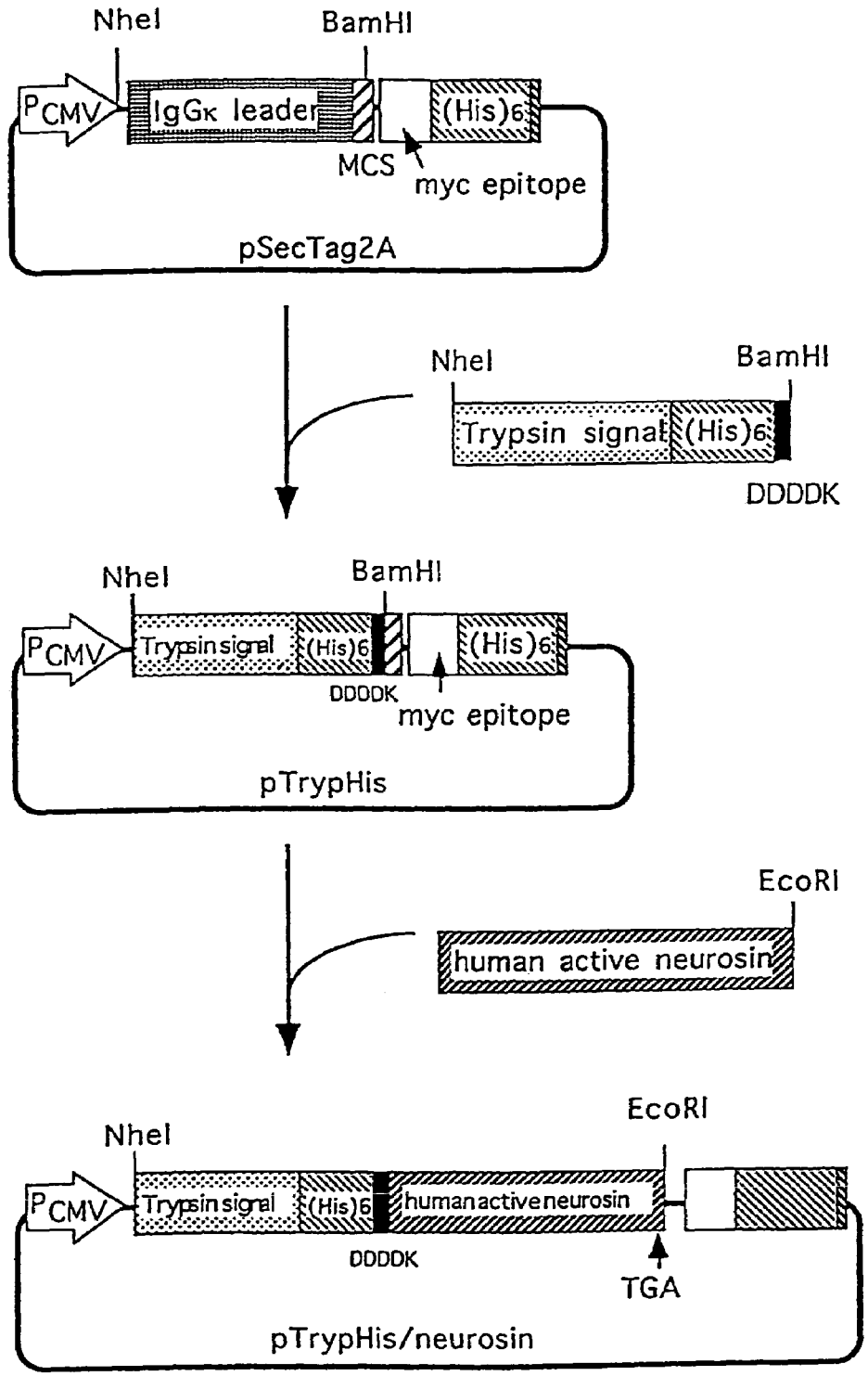
FIG. 1 illustrates construction of the plasmid pTrypHis/Neurosin produced by the process of Example 1.

The term "host cells" as used herein refers to cells, irrespective of the type, which express a nucleotide sequence encoding a target protein within the protein expression vector of the present invention and secrete the protein extracellularly. Therefore, the host cells may be microorganisms, preferably animal cells, and most preferably mammalian or insect cells.

Specific examples of mammalian cells and insect cells include human-derived cells, mouse-derived cells, fly-derived cells, silk worm-derived cells, and the like. In particular, the cells to be used are selected from the group consisting of CHO cells, COS cells, BHK cells, Vero cells, myeloma cells, HEK293 cells, HeLa cells, Jurkat cells, mouse L cells, mouse C127 cells, mouse FM3A cells, mouse fibroblast cells, osteoblasts, chondrocytes, S2 cells, Sf9 cells, Sf21 cells, High Five® cells, and the like. Also, microorganisms such as *Escherichia coli* and yeast may be used.

The "protein expression vector" of the present invention is preferably a vector which expresses a target protein as a recombinant fusion protein to facilitate isolation, purification or recognition. The term "recombinant fusion protein" refers to a protein, wherein an appropriate protein is attached to the N-terminus and/or the C-terminus of a target protein.

In this connection, the term "recombinant protein" is also used herein, and this refers to a recombinant fusion protein produced by integrating a nucleotide sequence encoding a target protein into the protein vector of the present invention and expressing the fusion protein from which an amino acid sequence derived from other than the nucleotide encoding the target protein is deleted by cleavage. Then, it is substantially a synonym of a target protein.

The protein expressed by the protein expression vector of the present invention and secreted extracellularly is a fusion protein comprising at least a target protein, a Tag sequence, and an amino acid sequence containing a cleavable site between the Tag sequence and the target protein. In addition, said fusion protein may further contain an epitope that can be recognized by an antibody, or the Tag sequence may function as an epitope. The desired recombinant protein can be obtained by subjecting the thus-expressed recombinant protein to an appropriate processing.

After translation, an active protein may be obtained. Even when the resultant protein is not an active protein, it may be converted to an active protein by a variety of techniques. In many cases, a protein is first synthesized at the ribosomes in the cytoplasm as an inactive precursor (pro-form) which comprises an active protein bearing at the N-terminus thereof a peptide of about 15 to 60 amino acids responsible for secretion (secretory signal). The peptide region, which functions as a secretory signal, is concerned with the mechanism of passing through the cell membrane, and is removed by cleavage with a specific protease during the passage through the membrane (not always) to yield a mature protein. The peptide moiety which functions as a secretory signal has a broad hydrophobic region comprising hydrophobic amino acids in the middle of the sequence, and basic amino acid residues at a site close to the N-terminus. A secretory signal may be understood as a synonym of a signal peptide.

In addition, in some proteins, a peptide moiety which functions as a secretory signal is further attached to the N-terminus of an inactive precursor (pro-form), and such a protein is called as a prepro-protein (the prepro-form). For example, trypsin is present as a prepro-form immediately after translation into amino acids, as a pro-form after being secreted from cells, and is converted into active trypsin in the duodenum upon limited degradation by enteropeptidase or by self degradation. A pro-form from which an active protein region has been deleted is called a pro-region, a prepro-form from which a pro-form region has been deleted is called a pre-region, and a prepro-form from which an active protein region has been deleted is called a prepro-region.

The "secretory signal nucleotide sequence", which is one of the essential components of the protein expression vector of the present invention, refers to the nucleotide sequence encoding a secretory signal. Also, the "secretory signal" refers to the pro-region when a protein is expressed as a pro-form, and at least the pre-region or the prepro-region when a protein is expressed as a prepro-form. However, the secretory signal is not limited in so far as it is capable of secreting the intracellularly expressed protein, extracellularly. The secretory signal nucleotide sequence constructed within the protein expression vector of the present invention preferably encodes a secretory signal with a cleavage site at the C-terminus of the signal. When the sequence encodes a secretory signal that does not contain a cleavage site at the C-terminus, it is preferred to newly insert a nucleotide sequence encoding a cleavable site at the 3' end of said secretory signal nucleotide sequence. This is, for example, a trypsin signal represented by 1st to 23rd amino acids in SEQ ID NO: 19. At the C-terminus (19th to 23rd amino acids) of said sequence, there is Asp-Asp-Asp-Asp-Lys which is recognizable by enterokinase.

Since the secretory signals of eukaryotic cells are similar to those of prokaryotic cells, *Escherichia coli* and the like may be used as the host. Since the secretory signal has different extracellular secretory activities depending on the host, it is necessary to select a secretory signal appropriate to the host. Specific examples of secretory signals include IgG (κ) (or IgGk) signal (or leader) and trypsin signal, which exhibit particularly high secretory activities when insect cells or mammalian cells are used as the host cells. Other examples of secretory signals include BiP of flies (*Drosophila*), melitin of honeybees, α-factor of *Pichia pastoris*, PHO, and the like. When a trypsin signal is referred to herein, it may be constructed by either the 1st to 18th amino acids or the 1st to 23rd amino acids in SEQ ID NO: 19. Further, the secretory signal also includes, other than those exemplified above, their homologs and variants which are capable of secreting proteins extracellularly.

The "Tag nucleotide sequence", which is another essential component of the protein expression vector of the present invention, refers to a nucleotide sequence that encodes a Tag sequence. The "Tag sequence" refers to an amino acid sequence that is not derived from the nucleic acid encoding a target protein and is inserted in order to facilitate, when expressed, isolation, purification and recognition of the target protein. Therefore, such a Tag sequence may be, for example, an antigen or an epitope recognizable by an antibody. By retaining the recombinant fusion protein containing a Tag sequence in a substance capable of recognizing said Tag sequence, isolation and purification can be carried out easily.

As a specific example of the isolation and purification process, the recombinant protein may be isolated and purified by retaining the recombinant fusion protein obtained by the present invention in a substance capable of recognizing, for example, Tag sequence, followed by liberating the fusion protein to obtain the recombinant fusion protein, which is further reacted with an enzyme capable of recognizing and cleaving the cleavable sequence. The recombinant protein may also be isolated and purified by reacting the recombinant fusion protein of the present invention, while it is retained by a substance capable of recognizing Tag sequence, with an enzyme capable of recognizing and cleaving the cleavable sequence, without undergoing the liberation process.

Specific examples of Tag nucleotide sequences include a nucleotide sequence which encodes polyhistidine (PHIS; hereinafter also referred to as histidine Tag or His tag) comprising preferably six histidines ((His) 6). The recombinant fusion protein, which is obtained by expressing the PHIS-encoding nucleotide sequence using the protein expression vector of the present invention, contains PHIS as the Tag sequence. PHIS is absorbed, for example, by a nickel-chelating resin (ProBond®), which can be desorbed from said resin by pH variation or by adding EDTA or an imidazole substance. The recombinant fusion protein can be isolated and purified by utilizing such properties.

In another example, glutathione-S-transferase (GST) is used as a Tag sequence, wherein affinity chromatography is run by using a glutathione Sepharose 4B column capable of recognizing GST, after which the recombinant protein can be isolated and purified by adding glutathione to allow competitive binding.

In still another example, calmodulin binding peptide (CBP) may be used as a Tag sequence, wherein affinity chromatography is run by using a calmodulin affinity resin capable of recognizing CBP, after which the recombinant protein can be isolated and purified by the addition of EGTA.

In still another example, protein A is used as a Tag sequence, wherein affinity chromatography is run by using an IgG Sepharose 6FF column capable of recognizing protein A, after which the recombinant protein can be isolated and purified by a treatment such as pH variation.

The "cleavable nucleotide sequence", which is still another essential component of the protein expression vector of the present invention, refers to a nucleotide sequence, wherein after said nucleotide acid sequence is translated into the amino acid sequence, said amino acid sequence can be cleaved at immediate upstream and/or immediate downstream and/or in the middle thereof.

For example, a nucleotide sequence encoding an aminoacid sequence which is susceptible to enzyme-specific cleavage corresponds to this sequence. Examples thereof include as follows: a nucleotide sequence encoding the amino acid sequence of Asp-Asp-Asp-Asp-Lys (amino acid 19–23 of SEQ ID NO:19) (said amino acid sequence is recognized by enterokinase, and the recombinant fusion protein is cleaved at the C-terminus thereof); a nucleotide sequence encoding the amino acid sequence of Leu-Val-Pro-Arg-Gly-Ser (SEQ ID NO:20) (said amino acid sequence is recognized by thrombin, and the recombinant fusion protein is cleaved between Arg-Gly thereof); a nucleotide sequence encoding the amino acid sequence Ile-Glu-Gly-Arg (SEQ ID NO:21) (said amino acid sequence is recognized by factor Xa, and the recombinant fusion protein is cleaved at the C-terminus thereof); a nucleotide sequence encoding the amino acid sequence Glu-Asn-Leu-Tyr-Phe-Gln (SEQ ID NO:22) (said amino acid sequence is recognized by TEV (Tobacco Etch virus) protease, and the recombinant fusion protein is cleaved at the C-terminus thereof), and the like.

The cleavable nucleotide sequence may be constructed by utilizing a part or all of the nucleotide sequence encoding the secretory signal nucleotide sequence, the Tag nucleotide sequence or the target protein, with or without an appropriate nucleotide sequence being added to it.

The protein expression vector of the present invention contains, in addition to the above-described three essential components, a nucleotide sequence encoding a target protein or a cloning site into which said nucleotide can be inserted, in the 3' downstream side of the essential components. The nucleotide sequence encoding the target protein is not specifically limited and a nucleotide sequence encoding insulin, interferons, erythropoietin, mannan binding protein, conglutinin, neurosin, or the like may be used.

Any backbone vector may be used for the protein expression vector of the present invention as far as the above essential components are present, but it is desirable to use one which fits to the host cells. A backbone vector refers to a vector that is used as a source material such as pSecTag2A, pSecTag2B, pFastBAC1, or the like as described in the Examples. The backbone vector is not specifically limited as far as it is a vector capable of expressing proteins, examples of which include pBAD/His, pRSETA, pcDNA2.1, pTrcHis2A, pYES2, pBlueBac4.5, pcDNA3.1 and pSecTag2 manufactured by Invitrogen Corporation, pET and pBAC manufactured by Novagen Company, pGEM manufactured by Promega Biotec, pBluescript II manufactured by Stratagene Company, pGEX and pUC18/19 manufactured by Pharmacia Corporation, pRTE, pEBFP and pGAD GH manufactured by Clontech Company, and the like.

Furthermore, a promoter and/or enhancer may be derived from the backbone vector, or they may be replaced, added or deleted to fit the host as appropriate. Promoters or enhancers which may be used include, for example, T7, CMV, HSV TK, SV40, RSV, trc, BAD, TRE-minCMV, 5' LTR, GAL 1, AOX 1, lac, ADH 1, polyhedrin, metallothionein, actin 5C gene, and the like.

The protein expression vector of the present invention may further include, in addition to the above essential components, a "spacer nucleotide sequence". A spacer nucleotide sequence refers to a nucleotide sequence encoding a spacer sequence, and may be inserted at any site within the protein expression vector of the present invention. A spacer sequence is an amino acid sequence (usually composed of about 1 to 50 amino acids) which is different from any of the secretory signal, the Tag sequence, the epitope sequence and the target protein, and plays a role as an auxiliary mean capable of secreting the target protein as a result.

A space sequence may be, for example, a cleavable sequence from which the secretory signal, the Tag sequence and epitope can be cleaved by enzyme, or the like. In particular, in the case where there is a histidine Tag upstream of the target protein, inserting successively a prepro-region in the secretory signal and inserting the amino acid sequence Leu-Val-His-Gly-Lys-Leu (amino acid 24–29 of SEQ ID NO:19) as a spacer sequence to the C-terminus of the prepro-region are convenient for the cleavage by an enzyme, or the like, because the distance between the trypsin signal and the histidine Tag becomes larger.

The protein expression vector of the present invention may also contain a nucleotide sequence encoding an "antibody recognition epitope". An antibody recognition epitope refers to an antigen determinant that is recognized by the antibody and is a region which is capable of binding to the antibody. The antibody may be any of monoclonal antibody, polyclonal antibody, antiserum, and the like. In the case where an epitope is expressed in such a way that it is contained in the recombinant fusion protein, the expression of the recombinant fusion protein can be confirmed by using an antibody against said epitope, and the protein is isolated and purified easily by an antigen-antibody affinity column, and further the recombinant protein can be obtained by cleaving the protein at the cleavable site as needed. Examples of expressible epitopes include Xpress, thioredoxin, c-myc, V5, HA/c-myc, and the like.

Introduction of the above expression vectors into the host cells per se may be conducted by employing a conventional method which includes, for example, transfection by the lipopolyamine method, the DEAE-dextran method, Hanahan's method, the lipofectin method, the calcium phosphate method, microinjection, electroporation, and the like.

The present invention includes, in addition to the protein expression vector of the above composition, host cells that are transformed by said protein expression vector, the process for production of the recombinant fusion protein that expresses the recombinant fusion protein by cultivating said transformed host cells, the recombinant fusion protein obtained by the process of said production process, the process for production of the recombinant protein wherein the recombinant protein is produced from said recombinant fusion protein, and the recombinant protein obtained by said production method.

EXAMPLES

Figure 3:
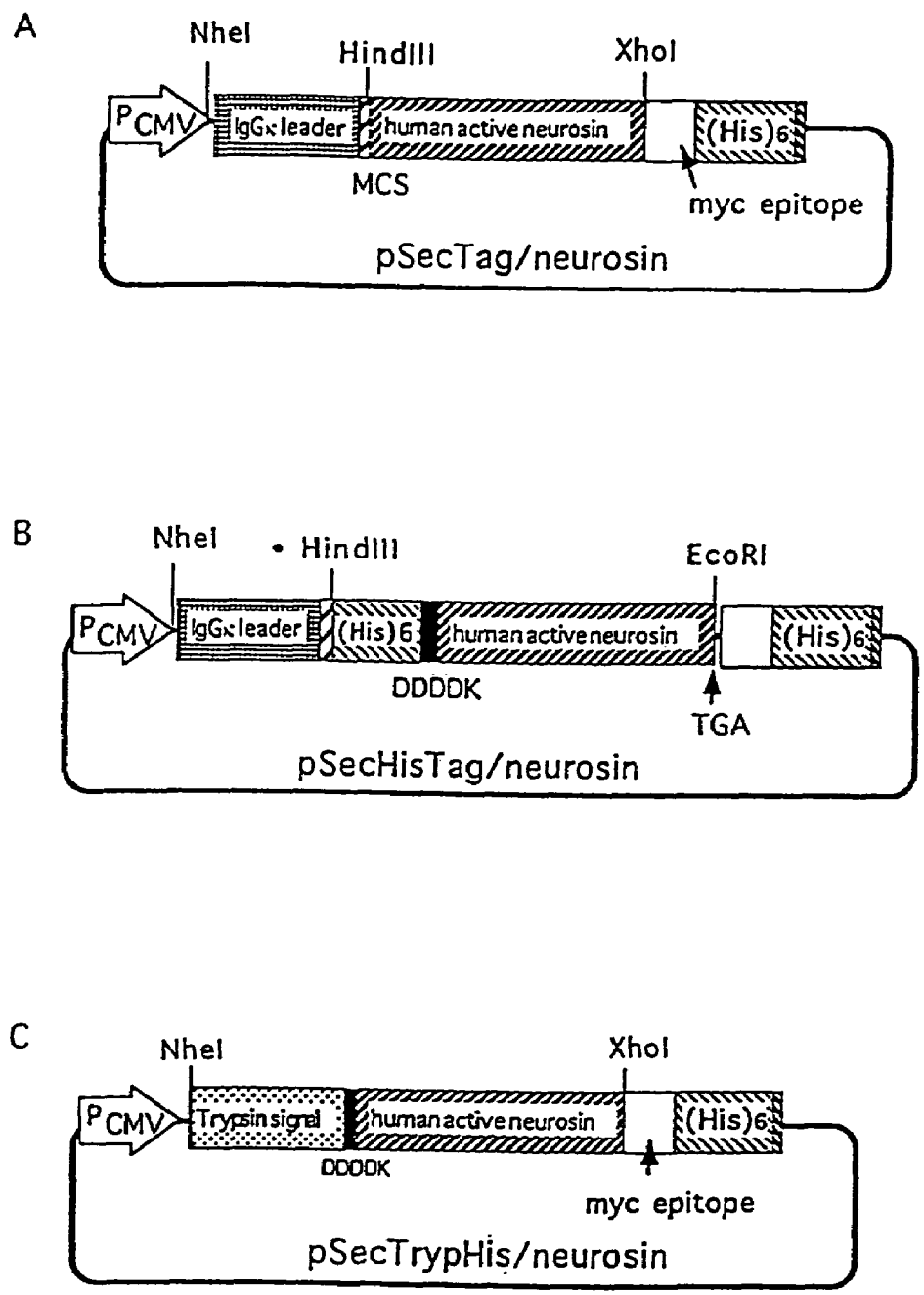
FIG. 3 illustrates construction of the plasmids pSecTag/Neurosin, pSecHisTag/Neurosin, and pSecTrypHis/Neurosin of Example 2.
Figure 5:
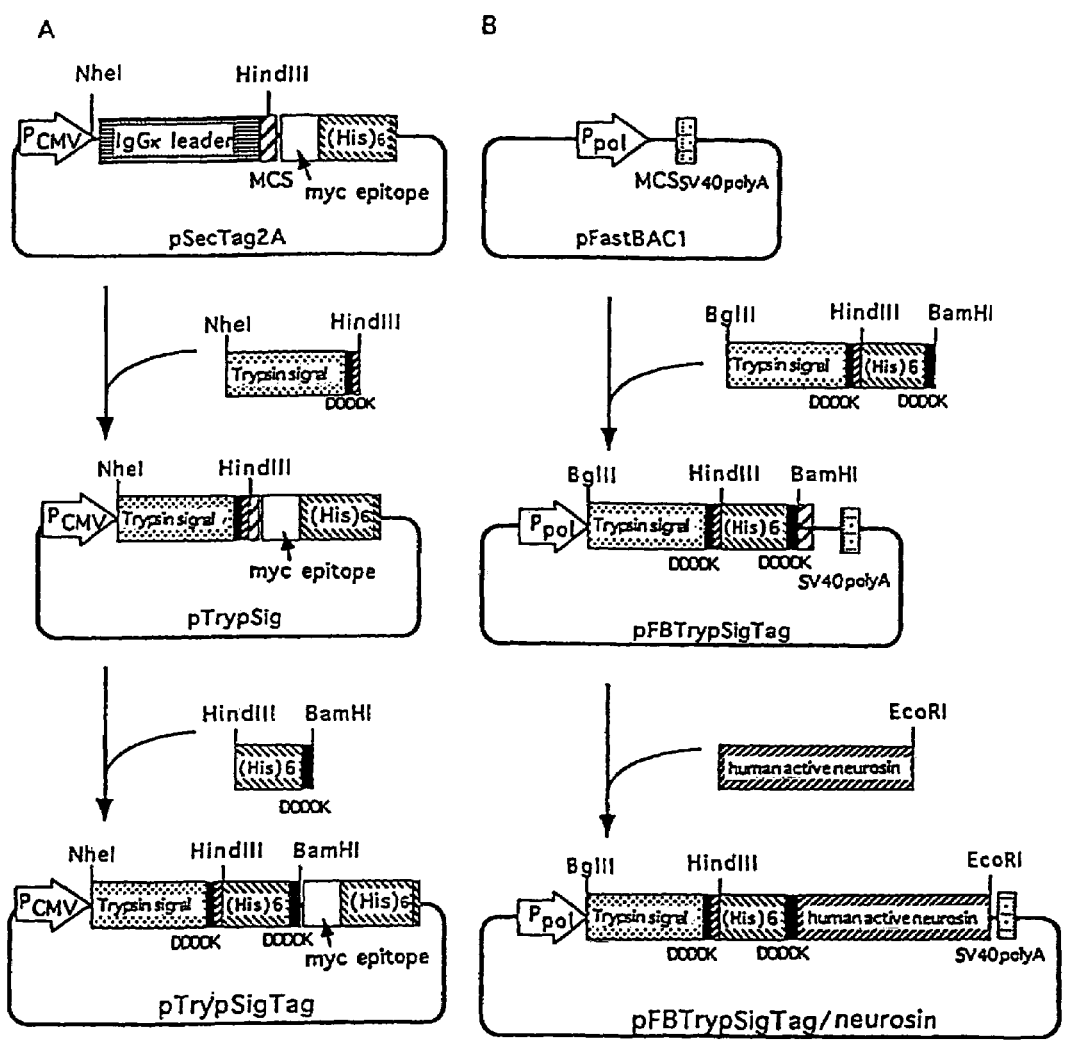
FIG. 5 illustrates construction of the plasmid pFB-TrypSigTag/Neurosin obtained by the process of Example 3.

The following Examples further illustrate the present invention in detail but are not to be construed to limit the scope of the present invention. In the following Examples, IgGk leader may be understood as a synonym of the secretory signal of IgG. When DDDDK (Asp-Asp-Asp-Asp-Lys) (amino acid 19–23 of SEQ ID NO:19) is present proximate to a trypsin signal, the DDDDK (amino acid 19–23 of SEQ ID NO:19) and the trypsin signal inclusive is called as trypsin signal in some cases (the sequence of 1st to 23rd amino acids in SEQ ID NO: 19), whereas only the trypsin signal without containing said DDDDK (amino acid 19–23 of SEQ ID NO:19) is as called trypsin signal (the sequence of 1st to 18th in SEQ ID NO:19) in other cases. Those skilled in the art can readily understand that a particular sequence corresponds to either of which from the context of the description. The trypsin signal shown in FIGS. 1, 3 and 5 refers to the 1st to 18th amino acids in SEQ ID NO: 19. In this connection, IgGk signal and the trypsin signal may be used in an interchangeable manner and, in this respect, both are considered to be equivalent, and the trypsin signal referred to herein may or may not include DDDDK.

Example 1

Construction and Expression of Plasmid pTrypTag/Neurosin

A sense DNA containing the nucleotide sequence shown in SEQ ID NO: 1 and an antisense DNA containing the nucleotide sequence shown in SEQ ID N: 2 were synthesized as a secretory signal containing a histidine Tag (His tag) (hereinafter referred to as His secretory signal) to be newly incorporated into the plasmid pSecTag2A (manufactured by Invitrogen Corporation). The sequences of the restriction site in this His secretory signal sequence were Hind III-Nhe I at the 5' end and BamH I-EcoR I at the 3' end.

Plasmid pSecTag2A (1 µg, 0.1 µl) was treated with the restriction enzymes Nhe I and BamH I to completely remove the region encoding IgGk leader sequence. To this solution were added 100 pmoles each of the sense DNA and the antisense DNA described above, and the mixture was treated at 70° C. for 10 minutes, after which it was left standing at room temperature for 30 minutes to allow annealing. To 1 µl each of the His secretory signal sequence, which had been treated with Nhe I and BamH I, and pSecTag2A was added 2.0 µl of solution I of DNA Ligation Kit Ver. 2 (Takara Shuzo Co., Ltd.), and the mixture was allowed to react at 16° C. for 30 minutes. To the reaction mixture was added 0.1 ml of competent *Escherichia coli* cells XL1-Blue (Stratagene Company), and the mixture was allowed to react on ice for 30 minutes, followed by heat shock at 42° C. for 60 seconds. After the reaction mixture was left on ice for 2 minutes, 0.9 ml of the SOC medium (Toyobo Co., Ltd.) was added and the cells were shake-cultured at 37° C. for one hour. The culture was centrifuged at 5,000 rpm for one minute and the supernatant was discarded. The sedimented competent cells were suspended in the solution remaining in the centrifugation tube, and applied to two ampicillin LB plates containing 100 µg/ml ampicillin at a ratio of 1:10. The cells were cultivated overnight at 37° C. and, from plasmids obtained from the resulting colonies, those with inserted DNA of the His secretory signal were selected by PCR and designated as pTrypHis.

pTrypHis was recovered by using a Pharmacia Flex Prep kit from *Escherichia coli* cells which were cultivated over day and night. To 5 μg of pTrypHis vector was added 20 units of BamH I and the vector was cleaved at 37° C. for 4 hours, after which 6 units of mung-bean exonuclease (Takara Shuzo Co., Ltd.) was added. The mixture was allowed to react at room temperature (25° C.) for 30 minutes to blunt the ends. Further, the 3' end of the cloning site was cleaved with 20 units of EcoR I, after which one unit of bacterial alkaline phosphatase (Takara Shuzo Co., Ltd.) was added. The mixture was reacted at 65° C. for 30 minutes. The inserted human neurosin cDNA was subjected to amplification by PCR by using the cDNA, which had already been cloned into pSPORT 1 (Gibco BRL), as the templates, at a portion corresponding to SEQ ID NOS: 3 and 4. In this case, the 5' end of SEQ ID NO: 3 was phosphorylated in advance by T4 polynucleotide kinase (Takara Shuzo, Co., Ltd.).

The thus-obtained PCR product was precipitated once by ethanol, after which the 3' end was cleaved by EcoR I. This cDNA and the above-mentioned pTrypHis were separated by electrophoresis on 1.0% agarose, and the target bands were cut out and purified by Sephaglas BandPrep kit (Pharmacia Corporation). They were then ligated in the same manner as described above and introduced into Escherichia coli XL1-Blue. Clones containing the sequence for neurosin were selected as pTRypHis/Neurosin (FIG. 1), and the plasmid DNA was recovered. One microgram of pTrypHis/Neurosin (1 μg) was introduced into COS-1 cells by using LipofectAMINE (Gibco BRL) according to the instruction manual. At 48 to 72 hours after introduction, the culture supernatant and the cell extract were recovered and subjected to western blot analysis using an anti-neurosin antibody (JP 10-187506 A) according to a conventional method, results of which demonstrated that the recombinant neurosin was present only in the cell extract (FIG. 2).

The nucleotide sequence and the amino acid sequence of human active-form neurosin are shown in SEQ ID NOS: 14 and 15.

Example 2

Studies on Preparation and Expression of pSecTag/Neurosin, pSecHisTag/Neurosin, and pSecTrypHis/Neurosin (1) Construction of each plasmid According to the same manner as in Example 1, cDNA corresponding to the active region of neurosin, which was amplified by SEQ ID NOS: 5 and 6 and using as the template pTrypHis/Neurosin, was inserted between Hind III site and Xho I site of pSecTag2B cloning site to obtain pSecTag/Neurosin (FIG. 3A). cDNA was amplified by using SEQ ID NOS: 7 and 4 and as the template pTrypHis/Neurosin constructed in Example 1, and was inserted between Hind III and EcoR I sites of pSecTag2B to obtain pSecHisTag/Neurosin (FIG. 3B). According to the same manner as in Example 1, SEQ ID NOS: 8 and 9 were annealed, and the fragment obtained by Nhe I and BamH I digestion was inserted into pSecTag2A to obtain pSecTrypHis. Into BamH I site and Xho I site of pSecTrypHis, which had been blunt-ended, was inserted active-form neurosin which had been amplified by SEQ ID NOS: 3 and 6 according to the same manner as in Example 1, to obtain pSecTrypHis/Neurosin (FIG. 3C).

The nucleotide sequence and amino acid sequence in upstream of cDNA of the region of active human neurosin in FIG. 3B, i.e, the region IgGk leader-spacer sequence-(His)6-DDDDK, are shown in SEQ ID NOS: 16 and 17. The IgGk leader corresponds to the 1st to 21st amino acids, the spacer sequence corresponds to the 22nd to 34th amino acids, (His)6 corresponds to the 35th to 40th amino acids, and DDDDK corresponds to the 41st to 45th amino acids.

(2) Expression of each plasmid in COS-1 cells

Figure 4:
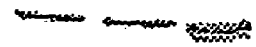
FIG. 4 illustrates the western blot analysis of the culture supernatant obtained in Example 2.

Each plasmid DNA (1 μg) was introduced into COS-1 cells according to the same method as in Example 1, and the cell extract and culture supernatant obtained after 48 to 72 hours were subjected to western blot analysis for the presence of recombinant neurosin protein by using an anti-neurosin antibody. The results demonstrated that neurosin was secreted into the culture supernatant in all of the supernatants studied, and that neurosin was secreted when at least the signal peptide and several amino acids at the C-terminus thereof were present. Also, there was no difference in secreting efficiency observed between the cases where the signal sequences of IgGk and trypsionogen are used (FIG. 4).

Example 3

Preparation of pFBTrypSigTag/Neurosin

The portion of pSecTrypHis/Neurosin spanning from the trypsin signal to the enterokinase recognition site was amplified by using SEQ ID NOS: 10 and 11 such that the peptide Leu-Val-His-Gly (amino acid 1–4 of SEQ ID NO;15) was located at the C-terminus. The product was inserted between Nhe I and Hind III sites of pSecTag2A to obtain the plasmid pTrypSig. About 200 bp which contained His tag region in pTrypHis was amplified by using SEQ ID NOS: 11 and 7. A fragment of about 40 bp containing His tag and enterokinase recognition site, which was produced by digesting with Hind III and BamH I, was inserted into pTrypSig to obtain pTrypSigTag (FIG. 5A).

cDNA, prepared by amplification of the portion from the trypsin signal sequence to the enterokinase recognition site of pTrypSigTag by PCR using SEQ ID NOS: 6 and 12, was cleaved out by Bg III and BamH I digestion, and inserted into BamH I site of pFastBac 1 (manufactured by Gibco Company). The direction of the insertion was confirmed by PCR using SEQ ID NOS: 6 and 13, and clones with the sequence inserted in the direction to be transcribed and translated by polyhedrin promoter were selected to obtain pFBTrypSigTag. To this was inserted the active form of neurosin according to the same manner as in Example 1 to obtain pFBTrypSigTag/Neurosin (FIG. 5B). In this case, the nucleotide sequence was determined by using a fluorescence-labeled SEQ ID NO: 10 to check whether or not neurosin was inserted correctly.

Figure 6:
FIG. 6 illustrates the western blot analysis of the culture supernatant obtained in example 3.

The nucleotide sequences and amino acid sequence of upstream of cDNA for the human active neurosin region in FIG. 5B, i.e., the nucleotide sequence and amino acid sequence of the region trypsin signal-DDDDK-spacer sequence-(His)6-DDDDK, are shown in SEQ ID NOS: 18 and 19. The trypsin signal-DDDDK corresponds to the 1st to 23rd amino acids, the spacer sequence corresponds to the 24th to 29th amino acids, (His)6 corresponds to 30th to 35th amino acids, and the succeeding DDDDK corresponds to 36th to 40th amino acids.

pFBTrypSigTag/Neurosin was processed according to the protocol of the Gibco BRL BAC-TO-BAC baculovirus expression system to obtain a recombinant bacmid containing on the bacmid DNA a chimeric neurosin-fused with the trypsinogen signal peptide, the His tag, and the enterokinase recognition site. When this bacmid was expressed in Sf-9 cells according to the manual of the BAC-TO-BAC baculovirus expression system, it was demonstrated by western blotting using an anti-neurosin antibody that neurosin was secreted in the culture supernatant from day 2 after viral infection (FIG. 6).

Western blotting may be carried out according to the following method. That is, after the culture supernatant was recovered, it was mixed with an equal volume of 2×SDS loading buffer (manufactured by Daiichi Pure Chemicals Co., Ltd.), and the mixture was heated in a boiling bath for 5 minutes to prepare a sample solution. The sample solution was subjected to electrophoresis on 10 to 20% polyacrylamide gel (manufactured by Daiichi Pure Chemicals Co., Ltd.) using an SDS electrophoretic apparatus (manufactured by Daiichi Pure Chemicals Co., Ltd.) and a SDS-tris-glycine buffer (manufactured by Daiichi Pure Chemicals Co., Ltd.). During the electrophoresis, two sheets of 3 MM filter paper (manufactured by Whatman Company) were immersed in the anolyte 1 (manufactured by Daiichi Pure Chemicals Co., Ltd.), one sheet in anolyte 2 (manufactured by Daiichi Pure Chemicals Co., Ltd.) and three sheets in a catholyte (manufactured by Daiichi Pure Chemicals Co., Ltd.). Also, a polyvinylidene difluoride-membrane (PVDF membrane: manufactured by Millipore Corporation) was immersed in methanol and then in distilled water to make it non-water repelling.

For the transfer of the proteins to the PVDF membrane, the gel was removed from the apparatus after the electrophoresis, and then on a blotter (manufactured by Pharmacia Company) were placed two sheets of filter paper immersed in buffer A from the anode, one sheet of filter paper immersed in buffer B, the PVDF membrane, the gel, and three sheets of filter paper immersed in buffer C in the order of description, whereby carrying out the transfer at 8 mV/cm$^2$ for 1.5 hours. After the transfer, the PVDF membrane was blocked by shaking in BlockAce (manufactured by Snow Brand Milk Products Co., Ltd.). Thereupon, said membrane was reacted overnight at 4° C. with an anti-neurosin antibody diluted with PBS containing 5% fetal bovine serum. Thereafter, alkaline phosphatase-labeled mouse IgG antibody was added and, after the reaction at room temperature for one hour, the color was developed with a NBT-BCIP solution to confirm the expression of the recombinant neurosin protein in the culture supernatant (FIG. 6).

Figure 7:
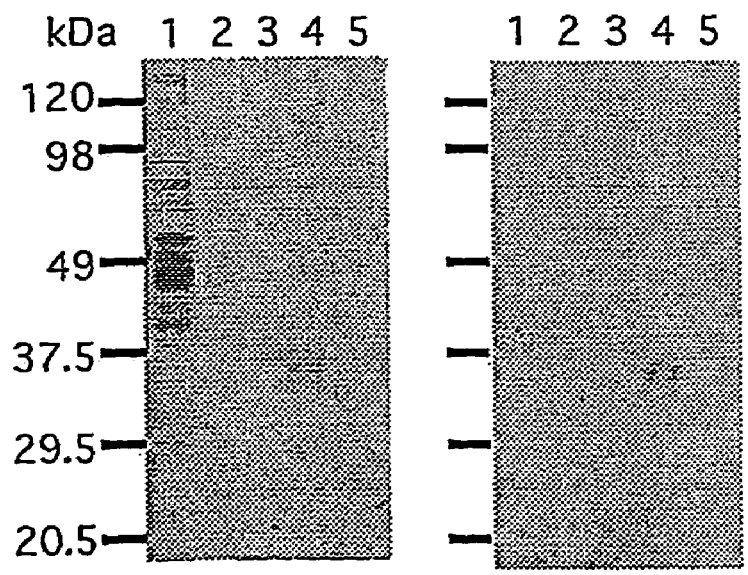
FIG. 7 illustrates a gel electrophoretic pattern of recombinant human neurosin purified by a nickel column.

Further, the recombinant fusion protein (neurosin) obtained in the culture supernatant was purified by passing through a chelate column, and assayed for the enzyme activity after dialysis. First, the culture supernatant was subjected to a chelate column (Ni-NTA-Agarose, manufactured by Qiagen Company) by using the PBS buffer, and eluted in a stepwise manner (5, 10, 100, 500 mM) with solutions of imidazole dissolved in —PBS (manufactured by Wako Pure Chemical Industries, Ltd.). Each fraction was subjected to electrophoresis and confirmed by the western blotting method and the Coomassie staining (FIG. 7). The western blotting was carried out according to the above described method, and Coomassie staining was carried out by immersing the electrophoresis gel in a solution of Coomassie brilliant blue for 10 minutes. Thereupon, the gel was destained in a destaining solution (water: acetic acid: methanol=33:6:21).

Figure 8:
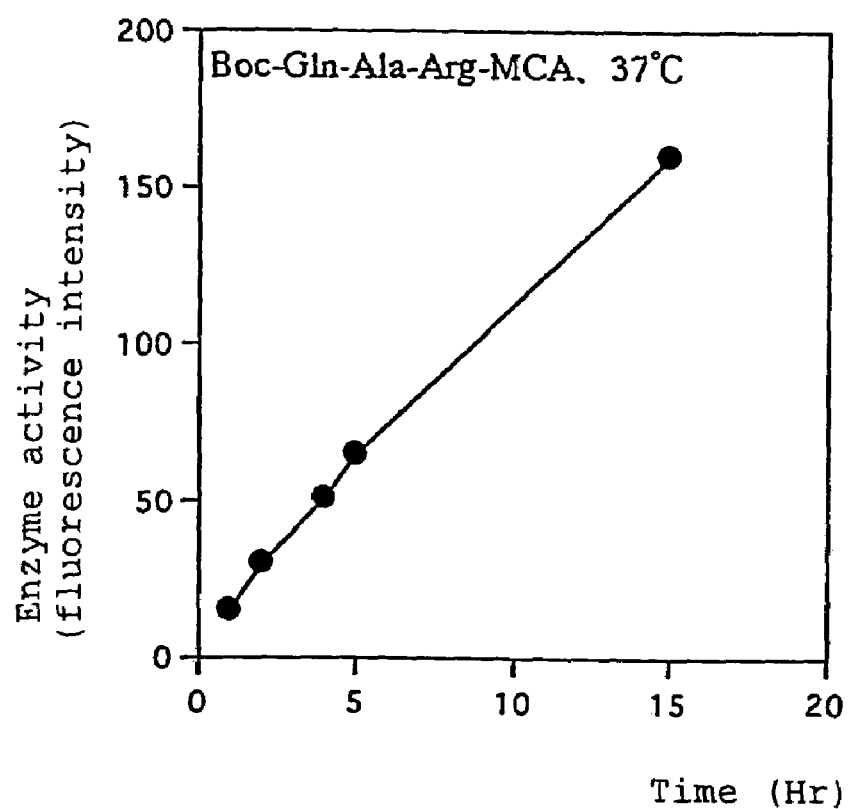
FIG. 8 illustrates the enzymatic activity of human neurosin expressed by using the baculovirus expression system.

The fraction obtained by eluting with 100 mM of imidazole was further replaced by the PBS buffer in a PD-10 column (manufactured by Pharmacia Company). Ten microliter of enterokinase (1 U/µl, manufactured by Invitrogen Corporation) was mixed with 50 µl of this sample, and the mixture was reacted at room temperature for 60 minutes. Next, 50 µl of a 0.2 M solution of a substrate, which was prepared by dissolving a synthetic substrate of Boc-Gln-Ala-Arg-MCA (Peptide Institute) in DMSO and by diluting in 1 M Tris-HCl (pH 8.0), was added and the mixture was reacted at 37° C. Fluorescence at an excitation wavelength of 380 nm and a fluorescence emission wavelength of 460 nm was determined sequentially (after 1, 2, 4, 5, and 15 hours) (FIG. 8). The values shown in the figure are those obtained after subtracting the fluorescence value of EK only.

INDUSTRIAL UTILITY

The protein expression vector of the present invention is advantageous and characterized by in that the protein expression vector has the above-described specific construction of the components thereby facilitating the purification and recovery of a target protein in a mature form or an active form. A preferred example of the construction of said protein expression vector includes a secretory signal nucleotide sequence, a Tag nucleotide sequence positioned in the 3' downstream thereof, a cleavable nucleotide sequence comprising a nucleotide sequence encoding the amino acid sequence of Asp-Asp-Asp-Asp-Lys (amino acid 36–40 of SEQ ID NO:19) capable of being recognized by enterokinase, a nucleotide sequence encoding the target protein positioned successively in the downstream, and a nucleotide sequence containing a stop codon positioned in the furthest downstream, where it is possible by using this vector to produce a recombinant protein without additional amino acids attached to the N-terminus or the C-terminus of the target protein, namely the target protein of a mature form or an active form.

Sequence Listing Free Text

SEQ ID NO: 1: Designed oligonucleotide to construct plasmid pTrpHis.

SEQ ID NO: 2: Designed oligonucleotide to construct plasmid pTrpHis.

SEQ ID NO: 3: Designed oligonucleotide primer to amplify neurosin-encoding sequence.

SEQ ID NO: 4: Designed oligonucleotide primer to amplify neurosin-encoding sequence.

SEQ ID NO: 5: Designed oligonucleotide primer to amplify a portion of plasmid pTRypHis/Neurosin.

SEQ ID NO: 6: Designed oligonucleotide primer to amplify a portion of plasmid pTrypHis/Neurosin.

SEQ ID NO: 7: Designed oligonucleotide primer to amplify a portion of plasmid pTrypHis/Neurosin.

SEQ ID NO: 8: Designed oligonucleotide to construct plasmid pSecTrypHis.

SEQ ID NO: 9: Designed oligonucleotide to construct plasmid pSecTrypHis.

SEQ ID NO: 10: Designed oligonucleotide primer to amplify a portion of plasmid pSecTryp/Neurosin.

SEQ ID NO: 11: Designed oligonucleotide primer to amplify a portion of plasmid pSecTryp/Neurosin.

SEQ ID NO: 12: Designed oligonucleotide primer to amplify a portion of plasmid pTrypSigTag.

SEQ ID NO: 13: Designed oligonucleotide primer to amplify a portion of plasmid pFBTrypSigTag.

What is claimed is:

1. A protein expression vector comprising (a) a nucleotide sequence encoding an IgG(κ) or a trypsin secretory signal peptide, (b) a nucleotide sequence encoding a polyhistidine amino acid sequence, (c) a nucleotide sequence encoding a polypeptide comprising amino acid residues 36–40 of SEQ ID NO:19 (Asp-Asp-Asp-Asp-Lys), wherein said polypeptide is cleavable by an enterokinase, and (d) a cloning site into which a polynucleotide encoding a target protein can be inserted, wherein:

(a), (b), (c) and (d) are assembled within the vector in the order recited;

the expression vector further comprises a polynucleotide encoding at least one amino acid residue, wherein said polynucleotide is located between the 3' end of the polynucleotide encoding the IgG(κ) or the trypsin secretory signal peptide and the 5' end of the polynucleotide having the nucleotide sequence of (c); and the polynucleotide encoding at least one amino acid residue is a polynucleotide encoding a polypeptide comprising amino acid residues 24–29 of SEQ ID NO:19 (Leu-Val-His-Gly-Lys-Leu).

2. A protein expression vector comprising (a) a nucleotide sequence encoding an IgG(K) or a trypsin secretory signal peptide, (b) a nucleotide sequence encoding a polyhistidine amino acid sequence, (c) a nucleotide sequence encoding a polypeptide comprising amino acid residues 36–40 of SEQ ID NO:19 (Asp-Asp-Asp-Asp-Lys), wherein said polypeptide is cleavable by an enterokinase, and (d) a cloning site into which a polynucleotide encoding a target protein can be inserted, wherein:

(a), (b), (c) and (d) are assembled within the vector in the order recited;

the expression vector further comprises a polynucleotide encoding at least one amino acid residue, wherein said polynucleotide is located between the 3' end of the polynucleotide encoding the IgG(K) or the trypsin secretory signal peptide and the 5' end of the polynucleotide having the nucleotide sequence of (c);

the polynucleotide encoding at least one amino acid residue comprises a nucleotide sequence encoding amino acids 3–40 of SEQ ID NO:19 (Asp-Asp-Asp-Asp-Lys).

3. A host cell transformed with the protein expression vector comprising (a) a nucleotide sequence encoding an IgG(K) or a trypsin secretory signal peptide, (b) a nucleotide sequence encoding a polyhistidine amino acid sequence, (c) a nucleotide sequence encoding a polypeptide comprising amino acid residues 36–40 of SEQ ID NO:19 (Asp-Asp-Asp-Asp-Lys), wherein said polypeptide is cleavable by an enterokinase, and (d) a cloning site into which a polynucleotide encoding a target protein can be inserted, wherein:

(a), (b), (c) and (d) are assembled within the vector in the order recited;

a polynucleotide encoding a target protein is inserted in the cloning site (d); and said host cell is an insect cell.

* * * * *